(12) United States Patent
Yamashita et al.

(10) Patent No.: US 10,791,940 B2
(45) Date of Patent: Oct. 6, 2020

(54) DIAGNOSIS ASSISTANCE APPARATUS, DIAGNOSIS ASSISTANCE METHOD, AND DIAGNOSIS ASSISTANCE PROGRAM

(71) Applicant: OMRON HEALTHCARE CO., LTD., Muko-shi, Kyoto (JP)

(72) Inventors: Shingo Yamashita, Muko (JP); Naoki Maeda, Muko (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 127 days.

(21) Appl. No.: 16/026,086

(22) Filed: Jul. 3, 2018

(65) Prior Publication Data

US 2018/0310837 A1    Nov. 1, 2018

Related U.S. Application Data

(63) Continuation of application No. PCT/JP2016/087286, filed on Dec. 14, 2016.

(30) Foreign Application Priority Data

Jan. 4, 2016 (JP) .................................. 2016-000169

(51) Int. Cl.
*A61B 5/02* (2006.01)
*A61B 5/021* (2006.01)
*A61B 5/00* (2006.01)

(52) U.S. Cl.
CPC ........ *A61B 5/02108* (2013.01); *A61B 5/6824* (2013.01); *A61B 5/7435* (2013.01)

(58) Field of Classification Search
CPC .. A61B 5/02108; A61B 5/7435; A61B 5/6824
See application file for complete search history.

(56) References Cited

U.S. PATENT DOCUMENTS

2004/0260192 A1    12/2004  Yamamoto
2006/0074327 A1     4/2006  Oshiumi et al.
(Continued)

FOREIGN PATENT DOCUMENTS

CN    1572238 A    2/2005
CN    1768700 A    5/2006
(Continued)

OTHER PUBLICATIONS

Jun. 7, 2018 International Preliminary Report on Patentability issued in International Patent Application No. PCT/JP2016/087286.
(Continued)

*Primary Examiner* — Amanda K Hulbert
*Assistant Examiner* — Natasha Patel
(74) *Attorney, Agent, or Firm* — Oliff PLC

(57) ABSTRACT

A diagnosis assistance apparatus acquires a predetermined period's worth of biological information measured from a living body every heartbeat, from a storage unit storing the biological information, divides the biological information into multiple segments, generates fluctuating state information indicating the fluctuating state of the biological information in each segment, and displays a graph indicating the fluctuating state information of each segment on a display unit. Furthermore, if a certain piece of fluctuating state information is selected in the graph displayed on the display unit, the diagnosis assistance apparatus displays a graph indicating the biological information belonging to the segment corresponding to the selected piece of fluctuating state information on the display unit.

12 Claims, 11 Drawing Sheets

(56) References Cited

U.S. PATENT DOCUMENTS

| | | | |
|---|---|---|---|
| 2009/0299199 A1 | 12/2009 | Kishimoto et al. | |
| 2010/0238192 A1* | 9/2010 | Kouchi | G01D 7/02 |
| | | | 345/593 |
| 2014/0221848 A1 | 8/2014 | Nagasaka | |
| 2016/0030804 A1* | 2/2016 | Mizuochi | A61B 5/11 |
| | | | 482/8 |
| 2016/0100766 A1* | 4/2016 | Yoshioka | G01S 13/88 |
| 2018/0199893 A1* | 7/2018 | Hubner | A61B 5/7282 |

FOREIGN PATENT DOCUMENTS

| | | |
|---|---|---|
| CN | 101304685 A | 11/2008 |
| CN | 102755154 A | 10/2012 |
| CN | 103961080 A | 8/2014 |
| JP | S60-148543 A | 8/1985 |
| JP | H05-184551 A | 7/1993 |
| JP | H10-94528 A | 4/1998 |
| JP | H11-148845 A | 6/1999 |
| JP | 2000-139860 A | 5/2000 |
| JP | 2003-265417 A | 9/2003 |
| JP | 2004-321438 A | 11/2004 |
| JP | 2005-000409 A | 1/2005 |

OTHER PUBLICATIONS

Feb. 28, 2017 International Search Report issued International Patent Application No. PCT/JP2016/087286.
Jun. 12, 2020 Office Action issued in Chinese Patent Application No. 201680077752.5.

* cited by examiner

DIAGNOSIS ASSISTANCE APPARATUS, DIAGNOSIS ASSISTANCE METHOD, AND DIAGNOSIS ASSISTANCE PROGRAM

CROSS-REFERENCE TO RELATED APPLICATION(S)

This application is a continuation of PCT application No. PCT/JP2016/087286, which was filed on Dec. 14, 2016 based on Japanese Patent Application (No. 2016-000169) filed on Jan. 4, 2016, the contents of which are incorporated herein by reference.

BACKGROUND

Technical Field

The present invention relates to a diagnosis assistance apparatus, diagnosis assistance method, and a diagnosis assistance program.

Background Art

Biological information (e.g., blood pressure values, pulse rate, and the like) that is needed for diagnosis of a living body normally changes significantly over the course of a day. For this reason, in order to perform diagnosis or the like, biological information is intermittently measured from a measurement subject and stored.

The measurement data of the biological information measured intermittently in this manner is preferably presented to a doctor after being processed such that diagnosis is easy to perform.

For example, Patent Document 1 discloses an apparatus that assists diagnosis of arteriosclerosis by dividing pulse wave transfer speeds measured over a predetermined period into set segments, calculating an average value of the pulse wave transfer speed in each set segment, and displaying the average values along with the maximum values and the minimum values of the pulse wave transfer speed in the set segments.

Also, Patent Document 2 discloses a method of graphing and outputting transitions of a diagnosis index of a biological circulatory system calculated using blood pressure values and pulse rate. In this example, each month, 50 diagnosis indices are calculated based on measurement values obtained by performing 50 instances of measuring the blood pressure values and the pulse rate, and a bar graph indicating the range of variation of each of the 50 diagnosis indices is displayed for each measurement month.

Also, Patent Document 3 discloses an apparatus that obtains a representative value for multiple instances' worth of blood pressure information (systolic blood pressure, diastolic blood pressure, and average blood pressure) measured in one day and displays the average value of representative values of one month, the average value of representative values of one week, and a representative value of one day in the form of bar graphs.

With this apparatus, when a certain month is designated on the screen on which the monthly representative values are displayed, a transition is made to a screen on which the daily representative values included in that month are displayed, and when a week is designated on the screen on which the monthly representative values are displayed, a transition is made to a screen on which daily representative values included in that week are displayed. In this manner, with the apparatus disclosed in Patent Document 3, it is possible to easily check the representative values for the blood pressure information for each day in a certain period, and thus it is possible to contribute to diagnosis.

Also, Patent Document 4 discloses a system in which measurement data of biological information measured over a certain period is divided into set segments, a representative value (e.g., an average value) for the biological information in each set segment is calculated, and the calculated average values and measurement data are displayed in an overlapping manner. According to this system, even if the trend of change is difficult to understand with only the measurement data, the overall trend can be easily understood according to the representative values.

CITATION LIST

Patent Literature

Patent Document 1: JP 2004-321438A
Patent Document 2: JP 2000-139860A
Patent Document 3: JP S60-148543A
Patent Document 4: JP 2003-265417A Patent Documents 1 to 4, it is envisioned that the biological information is measured and recorded in long time intervals, such as units of minutes, hours, or days. However, if the biological information is measured in long time intervals in this way, when there is a significant change in the biological information in a period in which the biological information was not measured, the doctor cannot be made aware of this change. Also, through comparison of the biological information measured in long time intervals, it is difficult to accurately find out that a change in the biological information has occurred and to find out the cause thereof.

In view of this, if an apparatus that measures the biological information in units of heartbeats (e.g., every heartbeat or every multiple heartbeats) is used, it is possible for a doctor to accurately keep track of small changes in the biological information caused by the everyday life of a patient. However, measuring the biological information in units of heartbeats results in an enormous amount of measurement data.

If such an enormous amount of measurement data is used, being able to understand the trend of the measurement data of the measurement period overall is effective for diagnosis. For this reason, it is preferable that the measurement data is processed using a method illustrated in Patent Documents 1 to 4 and displayed.

On the other hand, the biological information in units of heartbeats is needed to understand the changes in the biological information in detail, and in some cases, a doctor wishes to check not only the overall trend of the measurement trend, but also the measurement data in a specific period in detail.

With the system disclosed in Patent Document 4, the overall trend of the measurement data and the details of the measurement data can be checked simultaneously. However, if the amount of measurement data is enormous, display of the measurement data becomes elaborate, making it difficult to check the details, and thus efficient diagnosis assistance cannot be realized.

The apparatuses disclosed in Patent Documents 1 and 3 and the method disclosed in Patent Document 2 do not give consideration to checking the unprocessed measurement data.

The present invention has been made in view of the foregoing circumstances, and aims to provide a diagnosis assistance apparatus, a diagnosis assistance method, and a diagnosis assistance program that can efficiently perform assistance of diagnosis based on biological information measured in units of heartbeats.

SUMMARY

A diagnosis assistance apparatus of the present invention includes: a fluctuating state information generation unit configured to acquire a predetermined period's worth of biological information measured from a living body every heartbeat or every plurality of heartbeats, from a storage unit storing the biological information, divide the acquired predetermined period's worth of biological information into a plurality of segments, and generate fluctuating state information indicating a fluctuating state of the biological information in each segment; and a display control unit configured to display the fluctuating state information for each segment on a display unit, wherein, if a certain piece of the fluctuating state information displayed on the display unit is selected, the display control unit sets the display range that is to be displayed on the display unit among the predetermined period's worth of biological information to be a range that includes the biological information belonging to the segment corresponding to the selected piece of the fluctuating state information, and the display control unit displays the biological information in the set display range on the display unit.

A diagnosis assistance method of the present invention includes: a fluctuating state information generation step of acquiring a predetermined period's worth of biological information measured from a living body every heartbeat or every plurality of heartbeats, from a storage unit storing the biological information, dividing the acquired predetermined period's worth of biological information into a plurality of segments, and generating fluctuating state information indicating a fluctuating state of the biological information in each segment; and a display control step of displaying the fluctuating state information for each segment on a display unit, wherein, in the display control step, if a certain piece of the fluctuating state information displayed on the display unit is selected, the display range that is to be displayed on the display unit among the predetermined period's worth of biological information is set to be a range that includes the biological information belonging to the segment corresponding to the selected piece of the fluctuating state information, and the biological information in the set display range is displayed on the display unit.

A diagnosis assistance program of the present invention is a diagnosis assistance program for causing a computer to execute: a fluctuating state information generation step of acquiring a predetermined period's worth of biological information measured from a living body every heartbeat or every plurality of heartbeats, from a storage unit storing the biological information, dividing the acquired predetermined period's worth of biological information into a plurality of segments, and generating fluctuating state information indicating a fluctuating state of the biological information in each segment; and a display control step of displaying the fluctuating state information for each segment on a display unit, wherein, in the display control step, if a certain piece of the fluctuating state information displayed on the display unit is selected, the display range that is to be displayed on the display unit among the predetermined period's worth of biological information is set to be a range that includes the biological information belonging to the segment corresponding to the selected piece of the fluctuating state information, and the biological information in the set display range is displayed on the display unit.

DESCRIPTION OF EMBODIMENTS

Hereinafter, an embodiment of the present invention will be described with reference to the drawings.

Figure 1:
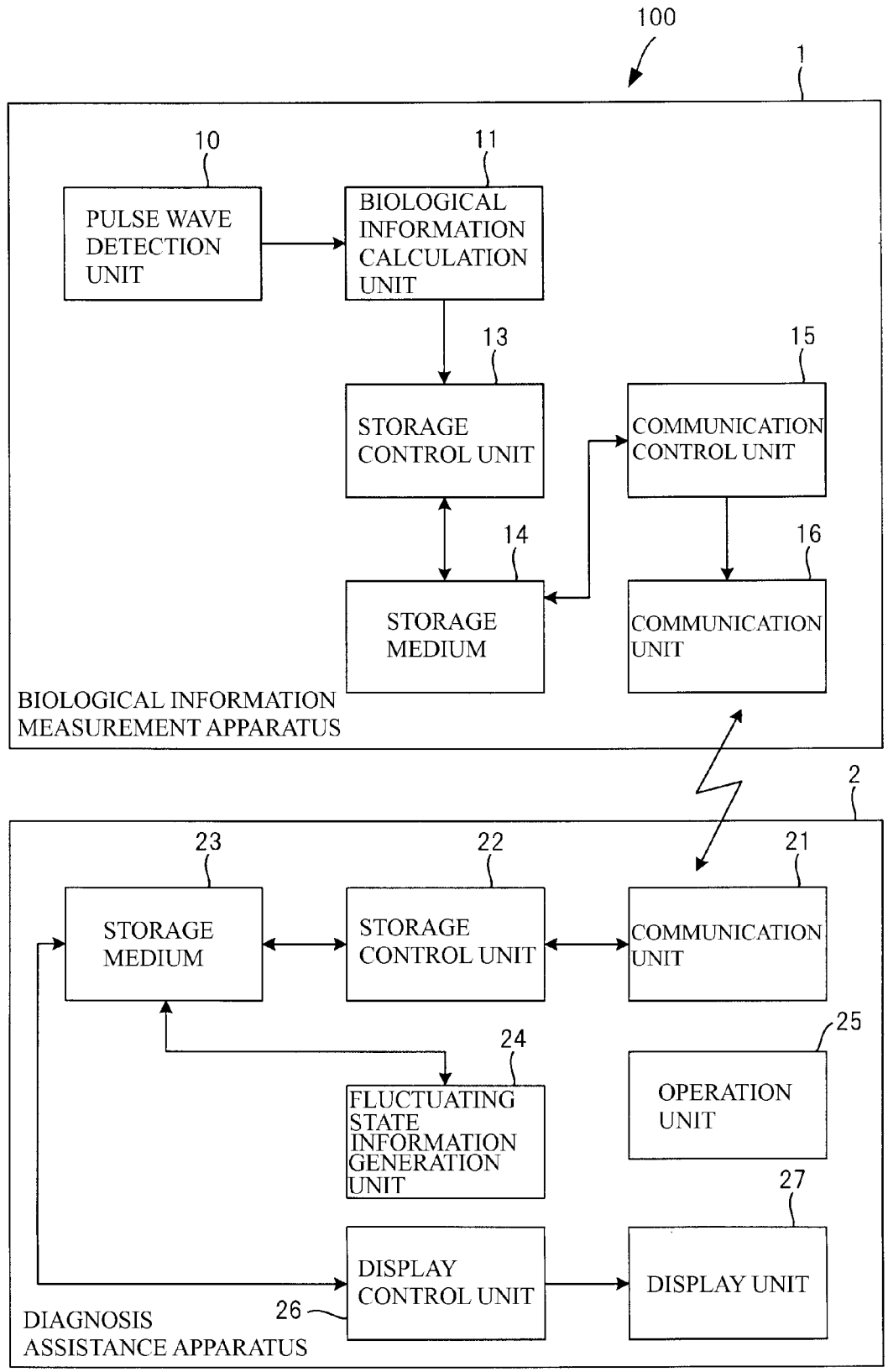
FIG. 1 is a diagram showing a schematic configuration of a diagnosis assistance system 100 for illustrating an embodiment of the present invention.

FIG. 1 is a diagram showing a schematic configuration of a diagnosis assistance system 100 for illustrating an embodiment of the present invention. The diagnosis assistance system 100 includes a biological information measurement apparatus 1 and a diagnosis assistance apparatus 2.

The biological information measurement apparatus 1 is portable and is used while worn on the wrist of a measurement subject serving as a living body.

The biological information measurement apparatus 1 includes a pulse wave detection unit 10, a biological information calculation unit 11, a recording control unit 13, a storage medium 14 such as a flash memory, a ROM (Read Only Memory) or a memory card, a communication control unit 15, and a communication unit 16. The storage medium 14 may be detachable from the apparatus.

The biological information calculation unit 11, the recording control unit 13, and the communication control unit 15 are functional blocks that are constituted by a processor executing a program.

The pulse wave detection unit 10 detects a pulse wave from the wrist of the measurement subject in a non-invasive manner.

A pulse wave detection unit 10 that detects a pressure pulse wave serving as a pulse wave through tonometry, for example, is used as the pulse wave detection unit 10. The pulse wave detection unit 10 may detect a volume pulse wave as the pulse wave. The pulse wave detection unit 10 may detect a pulse wave with reflected light from an artery, obtained by emitting light to the artery.

The pulse wave detection unit 10 detects a pulse wave generated for each heartbeat (a period in which the heart beats once) and transmits the detected pulse wave to the biological information calculation unit 11.

Based on the pulse wave detected by the pulse wave detection unit 10, the biological information calculation unit 11 calculates blood pressure information serving as the biological information for each heartbeat or for every multiple heartbeats (a frequency of once for multiple heartbeats).

The blood pressure information includes at least one of the systolic blood pressure (SBP), the diastolic blood pressure (DBP), and the mean blood pressure (MBP).

A known method can be used as the method for calculating the blood pressure information. The biological information calculation unit 11 transfers measurement data obtained by associating detection date/time information indicating the date and time of detecting a pulse wave and blood pressure information calculated based on the pulse wave, to the storage control unit 13.

The storage control unit 13 stores the measurement data transferred from the biological information calculation unit 11 in the storage medium 14.

Due to control performed by the storage control unit 13, multiple pieces of measurement data including the blood pressure information calculated by the biological information calculation unit 11 and detection time information indicating the time of detecting the pulse wave serving as the source of the blood pressure information are stored in the storage medium 14.

The communication unit 16 is an interface for performing communication with an external device through a wire or wirelessly.

The communication control unit 15 performs control for transmitting multiple pieces of measurement data stored in the storage medium 14 to an external device via the communication unit 16.

The diagnosis assistance apparatus 2 includes a communication unit 21, a storage control unit 22, a storage medium 23 such as a flash memory, a ROM, or a memory card, a fluctuating state information generation unit 24, an operation unit 25, a display control unit 26, and a display unit 27.

The storage medium 23 may be detachable from the diagnosis assistance apparatus 2. The storage medium 23 constitutes a storage unit.

The storage control unit 22, the fluctuating state information generation unit 24, and the display control unit 26 are functional blocks that are constituted by a processor executing a diagnosis assistance program.

The diagnosis assistance apparatus 2 may be a dedicated apparatus for diagnosis assistance or may be a general-purpose electronic device such as a smartphone or a tablet terminal.

The communication unit 21 is an interface for performing communication with an external device through a wire or wirelessly.

The display unit 27 displays various types of information for diagnosis assistance, and a display unit using a liquid crystal display element, an organic electroluminescence element, or the like is used thereas.

The display unit 27 need not be built into the diagnosis assistance apparatus 2 and may be provided outside of the diagnosis assistance apparatus 2 and connected through a wire or wirelessly to the diagnosis assistance apparatus 2.

The operation unit 25 is an interface for operating the diagnosis assistance apparatus 2.

The operation unit 25 is constituted by, for example, buttons provided on the diagnosis assistance apparatus 2, a keyboard and a mouse connected to the diagnosis assistance apparatus 2, a touch panel mounted on the display unit 27, or the like.

In a state in which communication between the communication unit 16 of the biological information measurement apparatus 1 and the communication unit 21 has been established, the storage control unit 22 performs a measurement data transmission request to the biological information measurement apparatus 1 via the communication unit 21.

The storage control unit 22 acquires the measurement data received by the communication unit 21 from the biological information measurement apparatus 1 according to the transmission request and stores the received measurement data in the storage medium 23.

The storage control unit 22 compares the measurement data stored in the storage medium 23 and the measurement data stored in the biological information measurement apparatus 1 and performs a request to transmit only new measurement data that has not been stored in the storage medium 23.

The fluctuating state information generation unit 24 acquires a predetermined period's worth of measurement data from among measurement data stored in the storage medium 23 and divides the acquired predetermined period's worth of measurement data into multiple segments.

As the predetermined period, a period (e.g., a specific day, a specific week, a specific time slot of a specific day, etc.) or the like set arbitrarily by a doctor operating the diagnosis assistance apparatus 2 is set through operation of the operation unit 25. Alternatively, a graph of the measurement data stored in the storage medium 23 may be displayed on the display unit 27 and a period selected through operation of the operation unit 25 in the displayed graph may be set as the predetermined period.

A "predetermined period's worth of measurement data" refers to measurement data in which times based on the detection time information belong to the predetermined period.

The method for dividing the measurement data will be described next.

For example, the fluctuating state information generation unit 24 selects 100 pieces at a time of the predetermined period's worth of measurement data in order starting from the earliest detection time, and divides the predetermined period's worth of measurement data into multiple segments using the period determined by the detection time information included in every selected 100 pieces of measurement data as one segment. Note that in some cases, there are less than 100 pieces of measurement data in the final segment among the multiple segments.

Alternatively, the fluctuating state information generation unit 24 successively selects one minute's worth of measurement information in the predetermined period's worth of measurement data in order starting from the earliest detection time, and divides the predetermined period's worth of measurement data into multiple segments using the period determined by the detection time information included in each selected one minute's worth of measurement data as one segment.

Figure 2:
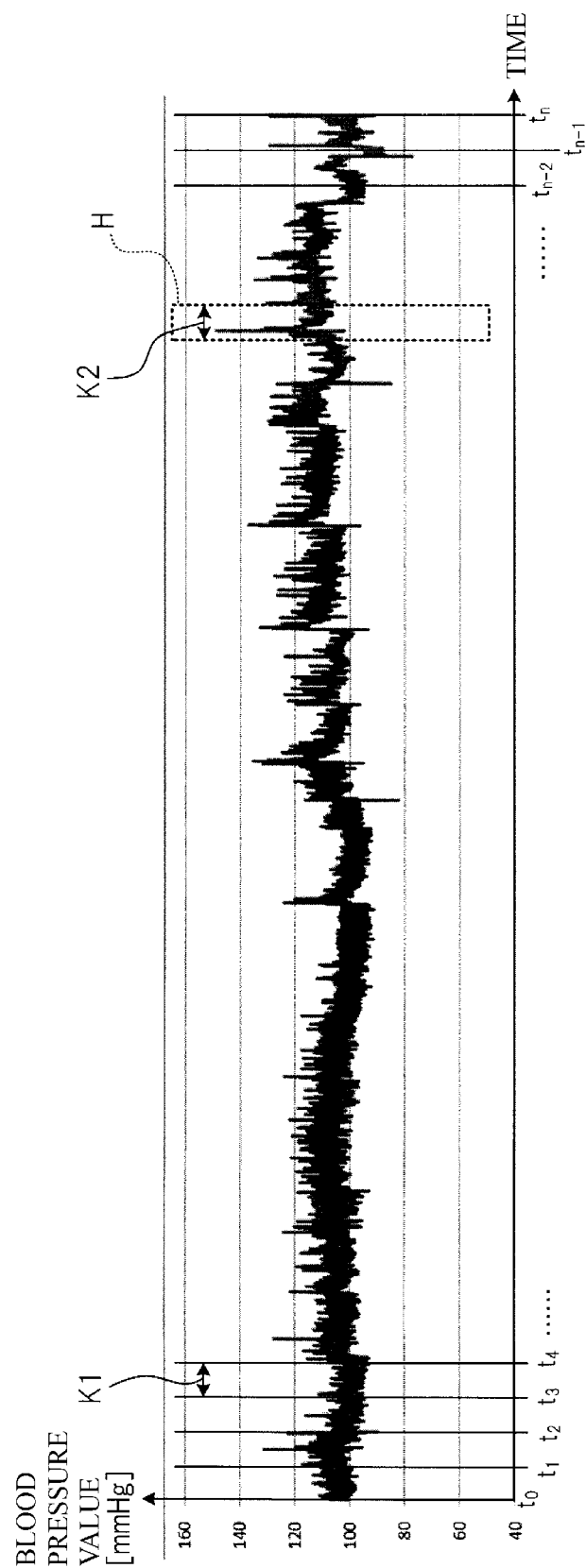
FIG. 2 is a diagram showing an example of a graph of a predetermined period's worth of measurement data.

FIG. 2 is a diagram showing an example of a graph of a predetermined period's worth of measurement data. The vertical axis in FIG. 2 indicates SBP as an example of the blood pressure information, and the horizontal axis indicates the detection time of the pulse wave used to calculate the SBP.

As shown in FIG. 2, the fluctuating state information generation unit 24 divides the predetermined period's worth of measurement data shown in FIG. 2 into multiple segments, using detection time $t_{k-1}$ (k=1, 2, 3, . . . , n) to detection time $t_k$ as one segment K1.

The fluctuating state information generation unit 24 stores the newest segment numbers in order starting from the earliest time in association with the multiple segments divided in this manner in the storage medium 23.

Furthermore, the fluctuating state information generation unit 24 generates fluctuating state information indicating the fluctuating state of the blood pressure information in a certain segment and stores the generated fluctuating state information in the storage medium 23 in association with the segment number of this certain segment.

The fluctuating state information generation unit 24 repeatedly performs processing for generating fluctuating state information, according to the number of types of blood pressure information.

In other words, the fluctuating state information generation unit 24 generates and stores the fluctuating state information for each segment with respect to a predetermined period's worth of SBPs, generates and stores the fluctuating state information for each segment with respect to a predetermined period's worth of DBPs, and generates and stores the fluctuating state information for each segment with respect to a predetermined period's worth of MBPs.

The fluctuating state information of the blood pressure information in a certain segment is constituted by the maximum value of the blood pressure information (SBP, DBP, or MBP) in that segment, the minimum value of the blood pressure information (SBP, DBP, or MBP) in that segment, and a representative value of the blood pressure information (SBP, DBP, or MBP) in that segment.

The representative value of the blood pressure information in a certain segment is a value indicating the overall trend of that segment, such as the average value of the blood pressure information in that segment, the mode of the blood pressure information in that segment, or the median of the blood pressure information in that segment.

The display control unit 26 displays, on a display unit 27, a first graph showing fluctuating state information for each segment stored in the storage medium 23. Due to control performed by the display control unit 26, a first graph illustrated in FIG. 3 is displayed on the display unit 27.

The fluctuating state information that can be displayed on the display unit 27 includes fluctuating state information generated regarding the SBP, fluctuating state information generated regarding the DBP, and fluctuating state information generated regarding the MBP.

With the diagnosis assistance apparatus 2, a configuration may be used in which it is possible to perform an instruction to simultaneously display multiple first graphs indicating fluctuating state information relating to multiple types of blood pressure information, and a configuration may be used in which it is possible to perform an instruction to display only a first graph indicating fluctuating state information relating to blood pressure information selected from among three types of blood pressure information.

Figure 3:
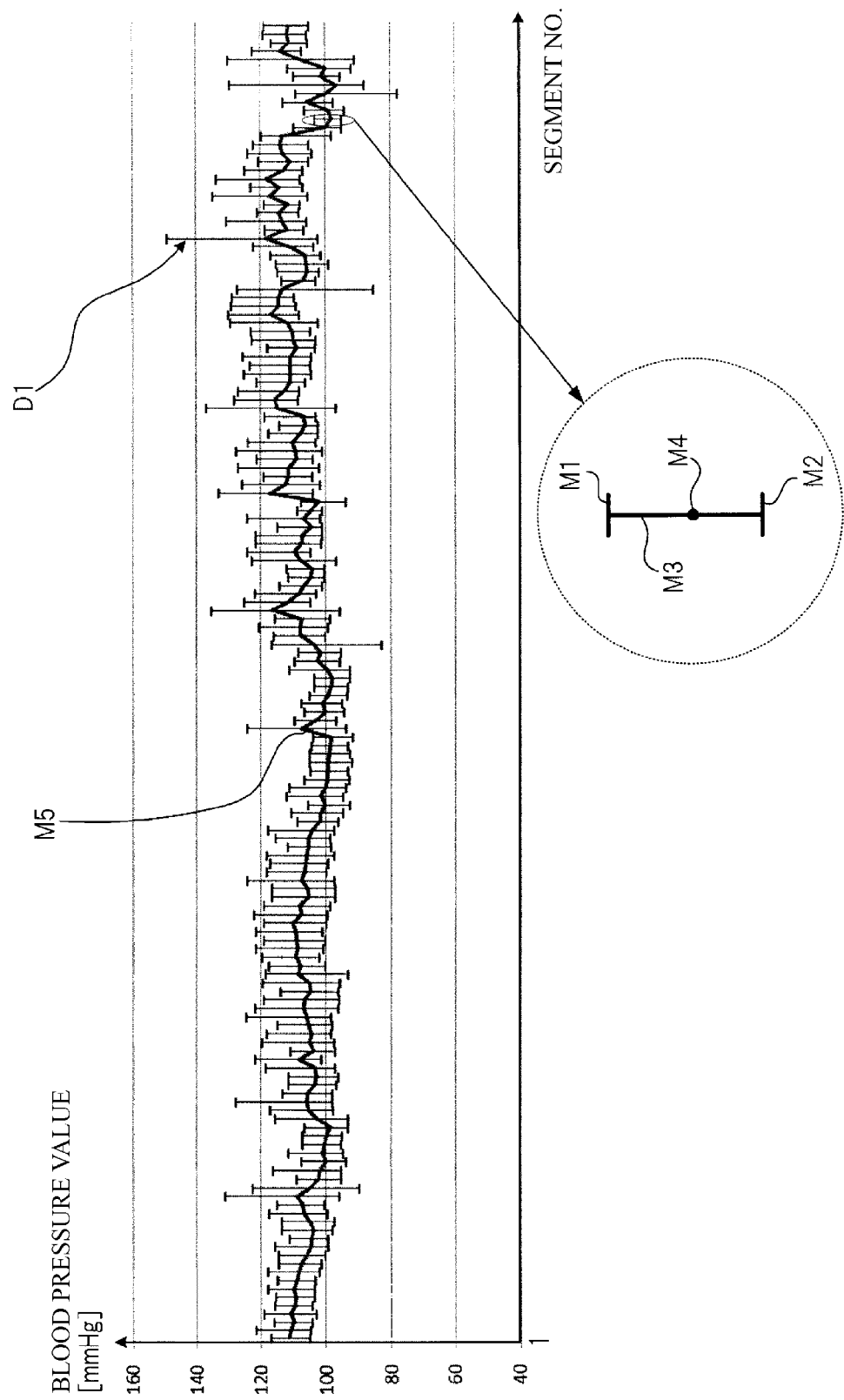
FIG. 3 is a diagram showing an example of display of a first graph showing fluctuating state information for each segment generated by a fluctuating state information generation unit 24 from the predetermined period's worth of measurement data shown in FIG. 2.

FIG. 3 is a diagram showing an example of display of a first graph showing fluctuating state information for each segment generated by the fluctuating state information generation unit 24 from the predetermined period's worth of measurement data shown in FIG. 2. The vertical axis in FIG. 3 indicates the blood pressure value—mmHg—and the horizontal axis indicates the segment number. FIG. 3 shows a first graph indicating fluctuating state information generated from the SBP.

The bottom portion of FIG. 3 shows an enlarged image showing fluctuating state information. This enlarged image is for description and is not displayed on the display unit 27.

The image showing the fluctuating state information included in the first graph is constituted by a horizontal bar M1 indicating the plot position of the maximum value of the SBP in the segment, a horizontal bar M2 indicating the plot position of the minimum value of the SBP in the segment, a vertical bar M3 linking the horizontal bar M1 and the horizontal bar M2, and a black circle mark M4 indicating the plot position of the average value of the SBP in the segment, which is overlaid on the vertical bar M3.

The image showing the fluctuating state information shown in FIG. 3 constitutes an image indicating the differences between the representative value of the blood pressure information in a segment and the maximum and minimum values.

Also, the first graph includes a curved line M5 that links the black circle marks M4 included in the images indicating the fluctuating state information corresponding to the segments.

By viewing the first graph shown in FIG. 3, a doctor can easily understand the overall trend of the SBP in a predetermined period due to the curved line M5.

Also, the doctor can easily keep track of the segments in which the SBP significantly fluctuates, according to the lengths of the vertical bars M3.

Furthermore, if the doctor focuses on one image indicating fluctuating state information, the doctor can more precisely understand the fluctuating state of the SBP in that segment according to the position of the black circle mark M4 on the vertical bar M3.

If the operation unit 25 is operated and one of the images indicating fluctuating state information (e.g., image D1 in FIG. 3) is selected while the first graph shown in FIG. 3 is displayed, the display control unit 26 sets the display range to be displayed on the display unit 27 among the predetermined period's worth of SBPs in FIG. 2, which is source data for the first graph shown in FIG. 3, to be a segment corresponding to the selected image D1, and displays a second graph indicating the SBPs in the set display range in a time series on the display unit 27.

FIG. 2 shows a display range H set by the display control unit 26. A width K2 in the time direction of the display range H is set to be the same as the width in the time direction of a segment K1.

If the image D1 is selected, the display control unit 26 sets the display range H to be a segment corresponding to the image D1 and performs enlarged display of a second graph indicating SBPs (i.e., SBPs belonging to the segment corresponding to the image D1) in the set display range in a time series on the display unit 27.

Figure 4:
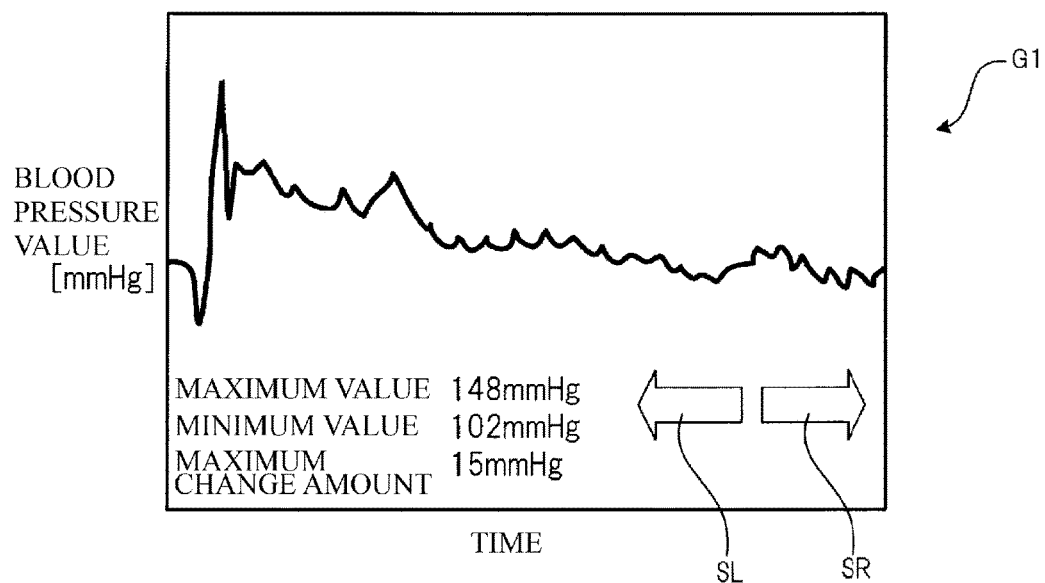
FIG. 4 is a diagram showing an example of display of a second graph showing blood pressure information in a display range H set by a display control unit 26.

FIG. 4 is a diagram showing an example of display of a second graph showing SBPs in a display range H set by the display control unit 26. As shown in FIG. 4, on the display unit 27, the display control unit 26 displays a second graph G1 obtained by enlarging the SBPs in the display range among the predetermined period's worth of SBPs shown in FIG. 2.

Also, the display control unit 26 displays the maximum value, the minimum value, and the maximum change amount of the SBPs in the display range H, along with the second graph G1. The maximum change amount is the value of the maximum difference between adjacent SBPs among the SBPs in the display range H.

Also, the display control unit 26 displays a scroll button SL and a scroll button SR for giving instructions to move the display range H, along with the second graph G1.

The scroll button SL is a button for giving an instruction to move the display range H set with respect to the predetermined period's worth of SBPs shown in FIG. 2, to the left side (in the direction of earlier detection times).

The scroll button SR is a button for giving an instruction to move the display range H set with respect to the predetermined period's worth of SBPs shown in FIG. 2, to the right side (in the direction of more recent detection times).

Note that the display control unit 26 may switch the screen to display the first graph shown in FIG. 3 and the second graph G1 shown in FIG. 4, but it is preferable to display the first graph shown in FIG. 3 and the second graph G1 shown in FIG. 4 together on the same screen.

By doing so, it is possible to understand the overall trend of the SBPs and the detailed SBPs in a desired segment without switching the screen, and thus diagnosis can be performed efficiently.

When an instruction to move the display range H is given by pressing the scroll button SL or the scroll button SR through operation of the operation unit 25, the display control unit 26 moves the display range H shown in FIG. 2 by a predetermined amount determined in advance, in a direction instructed according to the movement instruction.

When the scroll button SR is pressed once while the second graph G1 is displayed as shown in FIG. 4, the display control unit 26 moves the display range H by a predetermined amount in the right direction in FIG. 2.

During movement of the display range H, the SBPs in the display range H change successively, and therefore the display control unit 26 successively updates the second graph G1 to follow these changes.

Figure 5:
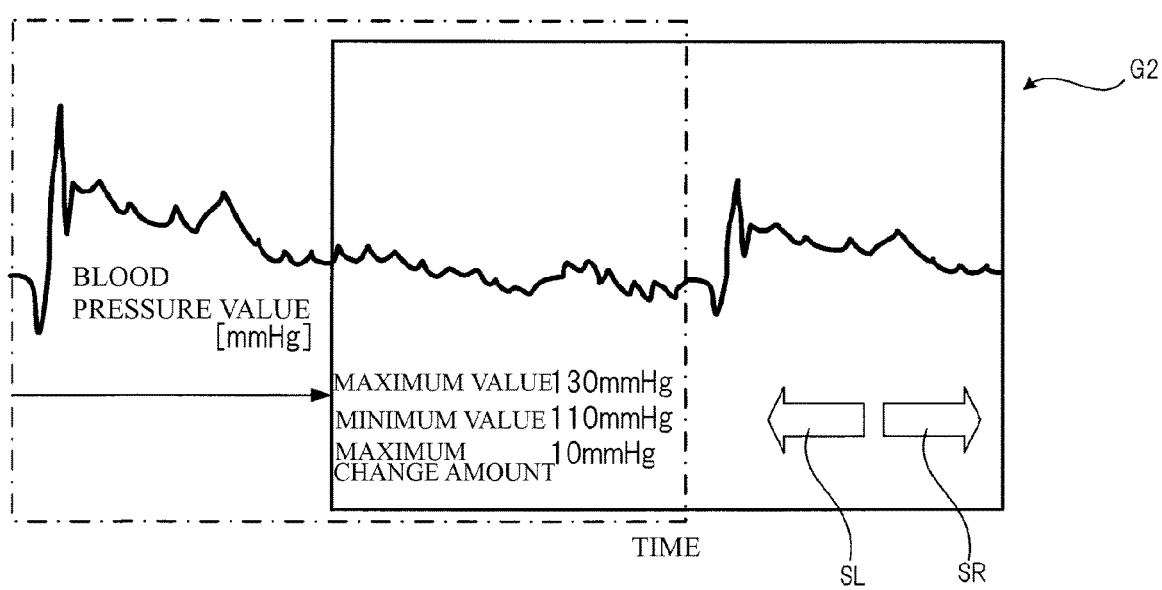
FIG. 5 is a diagram showing an example of display after a scroll button SR is pressed while a second graph G1 shown in FIG. 4 is displayed.

FIG. 5 is a diagram showing an example of display after a scroll button SR is pressed while a second graph G1 shown in FIG. 4 is displayed.

In FIG. 5, the graph in the rectangle indicated by the one-dot chain line is the second graph indicating the SBPs that were displayed before the display range H was moved. As shown in FIG. 5, due to the scroll button SR being pressed, the display range H moves rightward, and the second graph G1 is updated to be like the second graph G2.

In this manner, due to the SBPs being displayed through scrolling, a doctor can easily check the SBPs in the segments before and after the segment corresponding to the image D1 that was first selected, without once again selecting another image showing fluctuating state information. Accordingly, it is possible to efficiently perform determination of the cause of fluctuation in the SBPs.

Although it is sufficient that the movement amount (above-described predetermined amount) of the display range H in the case where the scroll button SR or the scroll button SL is pressed is any value, it is preferable to set it to a value that is smaller than the width K2 of the display range H (e.g., a value that is half or less of the width K2).

Doing so makes it possible to keep displaying the majority of the SBPs in the segment corresponding to the first-selected image D1 even if a scroll operation is performed, and thus diagnosis can be performed efficiently.

Next, operations performed by the diagnosis assistance apparatus 2 constituted as described above will be described with reference to a flowchart.

Figure 6:
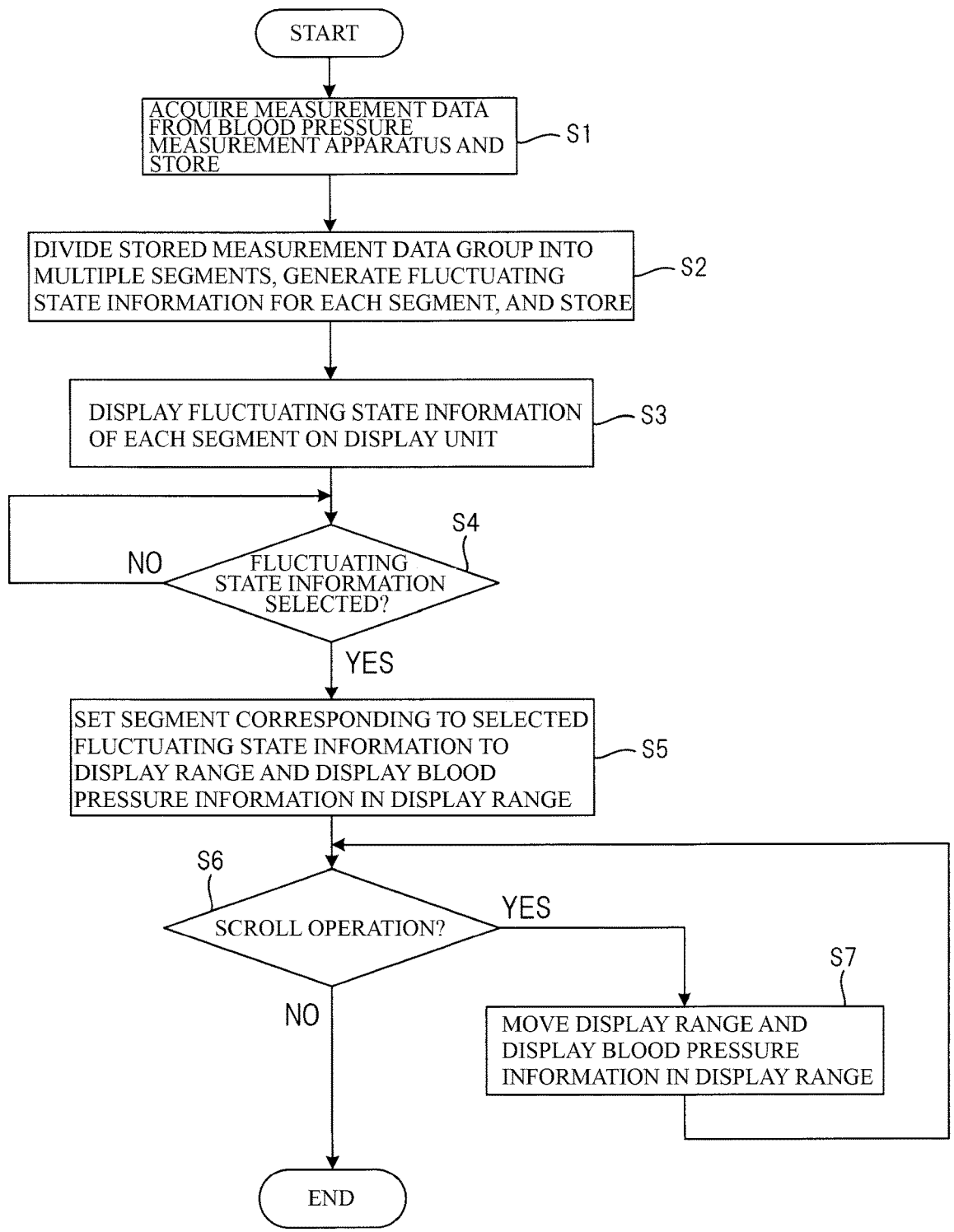
FIG. 6 is a flowchart for describing operations performed by a diagnosis assistance apparatus 2.

FIG. 6 is a flowchart for describing operations performed by the diagnosis assistance apparatus 2.

If the diagnosis assistance apparatus 2 can communicate with the biological information measurement apparatus 1 and an instruction to receive measurement data is performed by operating the operation unit 25, the storage control unit 22 acquires measurement data stored in the storage medium 14 of the bodily information measurement apparatus 1 and stores the acquired measurement data in the storage medium 23 (step S1).

Next, the fluctuating state information generation unit 24 divides the predetermined period's worth of measurement data (measurement data group) stored in the storage medium 23, generates fluctuating state information for each segment, and stores the generated fluctuating state information in the storage medium 23 (step S2).

Next, the display control unit 26 displays, on a display unit 27, a first graph showing fluctuating state information for each segment stored in the storage medium 23 (step S3).

Next, the display control unit 26 determines whether or not a piece of fluctuating state information included in the first graph being displayed has been selected (step S4).

If it is determined that no fluctuating state information has been selected (step S4: NO), the display control unit 26 repeats the processing of step S4, and if it is determined that fluctuating state information has been selected (step S4: YES), the display control unit 26 performs the processing of step S5.

In step S5, the display control unit 26 sets the segment corresponding to the selected fluctuating state information as the display range and performs enlarged display of the second graph showing the blood pressure information in the set display range in a time series on the display unit 27.

Next, the display control unit 26 determines whether or not the scroll button SR or the scroll button SL was pressed during display of the second graph (step S6).

If it is determined that neither the scroll button SR nor the scroll button SL was pressed (step S6: NO), the display control unit 26 ends the processing.

If it is determined that the scroll button SR or the scroll button SL was pressed (step S6: YES), the display control unit 26 moves the display range according to the scroll instruction and performs enlarged display of the blood pressure information in the display region (step S7). After step S7, the processing returns to step S6.

As described above, according to the diagnosis assistance apparatus 2, the overall trend of the blood pressure information of the measurement subject can be easily understood using the first graph shown in FIG. 3, which is displayed based on an enormous amount of blood pressure information measured every heartbeat or every multiple heartbeats from the measurement subject.

Also, by selecting the fluctuating state information included in the first graph, it is possible to check a second graph obtained by enlarging the blood pressure information of the segment corresponding to that fluctuating state information. For this reason, it is possible to instantaneously understand the details of the blood pressure information of a segment with significant fluctuation, and it is possible to efficiently perform diagnosis.

Also, the scroll button SR and the scroll button SL are displayed along with the second graph shown in FIG. 4, and by pressing the scroll button SR or the scroll button SL, it is possible to arbitrarily move the display range of the blood pressure information. In this way, the details of the blood pressure information of the segments before and after the segment with significant fluctuation can also be checked instantaneously, and therefore it is possible to efficiently perform diagnosis.

In the foregoing description, the width K2 of the display range set by the display control unit 26 was the same as that of each segment K1 obtained by dividing the predetermined period's worth of blood pressure information. In a modified example, the width K2 of the display range may be made wider than the width of the segment K1.

For example, the display control unit 26 may set a total of three segments, namely the selected segment, the segment prior thereto, and the segment following thereafter, as the display range, or may set a total of two segments, namely the selected segment, and the segment prior thereto or the segment following thereafter, as the display range. In other words, the width K2 of the display range may be twice or three times the width of the segment K1.

Thus, the blood pressure information of not only the segment selected by the doctor, but also of a segment adjacent to that segment is subjected to enlarged display, whereby it is possible to instantaneously find out the state of the blood pressure before and after a blood pressure fluctuation occurs, and therefore it is possible to contribute to diagnosis.

It is preferable that the display control unit 26 of the diagnosis assistance apparatus 2 determines the degree of similarity between fluctuating state information of a segment adjacent to the segment (also called "displayed segment") including the information being displayed as the second graph and the selected fluctuating state information, and if there is an adjacent segment with a degree of similarity greater than or equal to a threshold, the display control unit 26 displays information for performing notification of the direction of the adjacent segment along with the second graph.

For example, an exemplary case is given in which the second graph G1 shown in FIG. 4 is displayed due to the image D1 being selected on the first graph shown in FIG. 3.

In this case, the display control unit 26 determines a first similarity degree between the fluctuating state information corresponding to the segment adjacent to the right of the segment (displayed segment) corresponding to the image D1 shown in FIG. 3 and the fluctuating state information displayed in the image D1, and a second similarity degree between the fluctuating state information corresponding to the segment adjacent to the left of the segment (displayed segment) corresponding to the image D1 shown in FIG. 3 and the fluctuating state information displayed in the image D1.

If the difference between the maximum values of the blood pressure information included in the two pieces of fluctuating state information corresponding to the two segments whose degree of similarity is to be determined is less than or equal to a similarity threshold, the display control unit 26 determines that the degree of similarity of the fluctuating state information corresponding to the two segments is greater than or equal to a threshold. If the above-described difference exceeds the similarity threshold, the display control unit 26 determines that the degree of similarity of the fluctuating state information corresponding to the two segments is less than a threshold.

Alternatively, if the difference between a value obtained by subtracting the minimum value from the maximum value of the blood pressure information included in the fluctuating state information corresponding to one of the two segments whose degree of similarity is to be determined, and a value obtained by subtracting the minimum value from the maximum value of the blood pressure information included in the fluctuating state information corresponding to the other of the two segments, is less than or equal to a similarity threshold, the display control unit 26 determines that the degree of similarity of the fluctuating state information corresponding to the two segments is greater than or equal to a threshold. If the above-described difference exceeds the similarity threshold, the display control unit 26 determines that the degree of similarity of the fluctuating state information corresponding to the two segments is less than the threshold.

In this manner, the display control unit 26 determines whether or not there is an adjacent segment associated with fluctuating state information that is similar to the fluctuating state information corresponding to the selected segment, among the adjacent segments adjacent to the displayed segment including the blood pressure information being displayed as the second graph (the display control unit 26 determines whether or not there is an adjacent segment with a high degree of similarity to the selected segment).

If it is determined that there is an adjacent segment with a high degree of similarity to the selected segment, the display control unit 26 displays information for performing notification of the direction of the adjacent segment for which it was determined that the degree of similarity was high, along with the second graph.

Figure 7A:
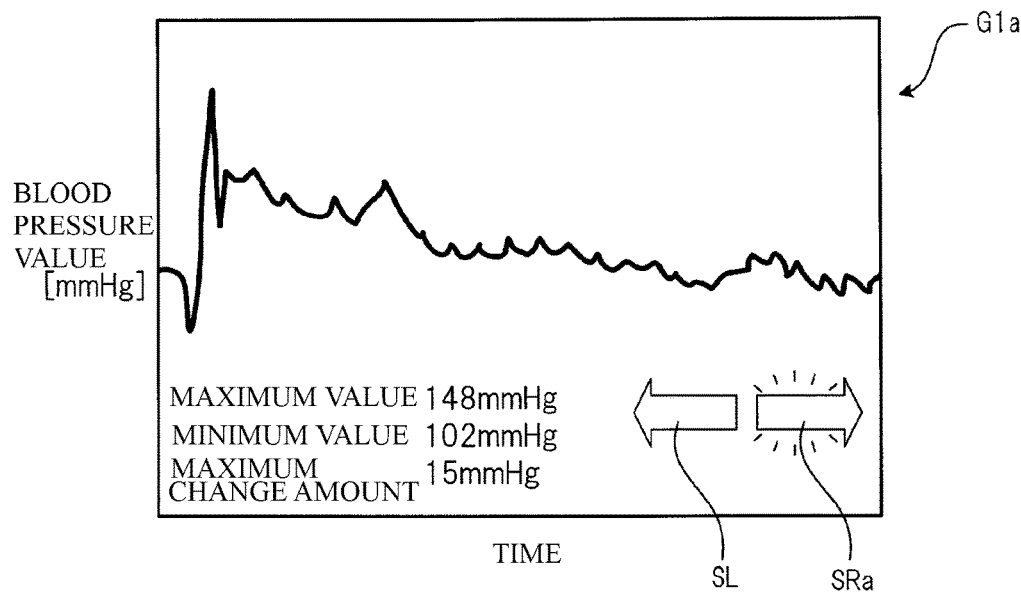
FIGS. 7A and 7B are diagrams each of which shows an example of display of a second graph in a case in which it is determined that a degree of similarity of a segment adjacent to the right of a segment being displayed is high.
Figure 7B:
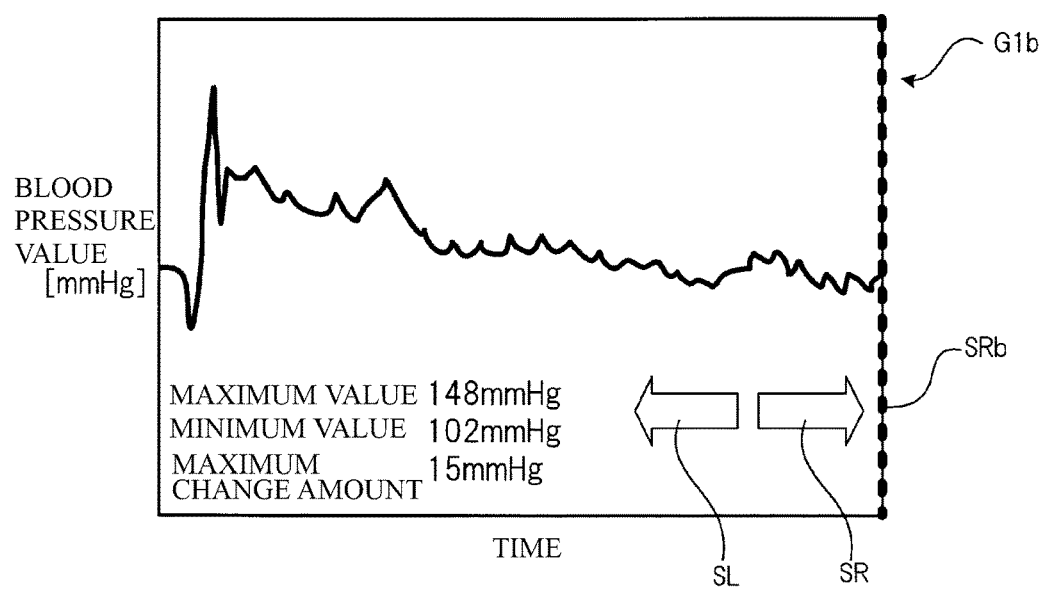

FIGS. 7A and 7B are diagrams each of which shows an example of display of a second graph in a case in which it is determined that the degree of similarity of the segment adjacent to the right of the segment being displayed is high.

A second graph G1*a* shown in FIG. 7A is obtained by changing the scroll button SR to a scroll button SRa in the second graph G2 shown in FIG. 4.

The scroll button SRa is displayed in an emphasized manner by causing the scroll button SR to blink or changing the display color thereof to a color that is different from that of the scroll button SL.

Thus, if it is determined that the degree of similarity of the segment adjacent to the right of the displayed segment is high, the display control unit 26 displays the scroll button SRa as information for performing notification of the rightward direction.

The second graph G1*b* shown in FIG. 7B is obtained by adding a broken line SRb to the right edge of the graph in the second graph G2 shown in FIG. 4.

Thus, if it is determined that the degree of similarity of the segment adjacent to the right of the displayed segment is high, the display control unit 26 displays the broken line SRb as information for performing notification of the rightward direction.

According to the description above, if there is an adjacent segment with a high degree of similarity to the selected segment, notification of the direction of the adjacent segment is performed as shown in FIGS. 7A and 7B, and thus it is possible to effectively assist diagnosis.

For example, a case will be considered in which fluctuating state information indicating a large maximum value of the blood pressure information is selected first. In this case, it is thought that the doctor will give attention to a segment in which the blood pressure information is large.

For this reason, if there is a segment in which the maximum value of the blood pressure information is large, similarly to the selected segment, it is highly likely that the doctor will want to check the details of the blood pressure information for that segment as well. Accordingly, by performing notification of the direction of an adjacent segment in which the blood pressure information indicates a trend similar to that of the selected segment, it is possible to efficiently perform diagnosis.

Note that if the blood pressure information is displayed spanning over two segments as shown in FIG. 5 due to a scroll operation, the display control unit 26 determines the degree of similarity between the segment adjacent to the right of the more recent segment among the two segments being displayed and the segment corresponding to the image D1, and if the degree of similarity is greater than or equal to a threshold, the display control unit 26 displays a broken line indicated in FIG. 7B on the right edge of the second graph, for example.

Also, the display control unit 26 determines the degree of similarity between the segment adjacent to the left of the earlier segment (segment corresponding to the image D0 among the two segments being displayed and the segment corresponding to the image D1, and if the degree of similarity is greater than or equal to a threshold, the display control unit 26 displays the broken line shown in FIG. 7B on the left side of the second graph G2, for example. Accordingly, even if the scroll operation is performed, the doctor can be notified of whether or not there is a segment with a high degree of similarity and of its direction.

Figure 8:
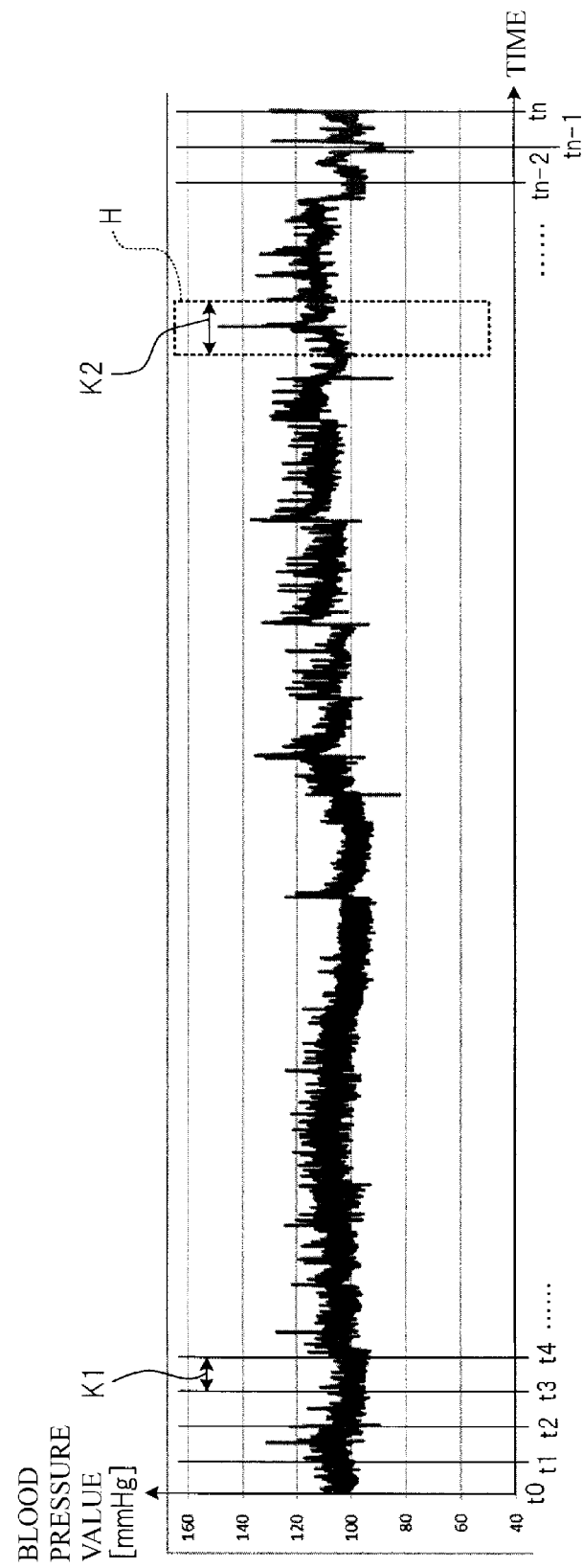
FIG. 8 is a diagram showing an example in which a width K2 of the display range set by the display control unit 26 is made wider than the width of a segment K1.
Figure 9:
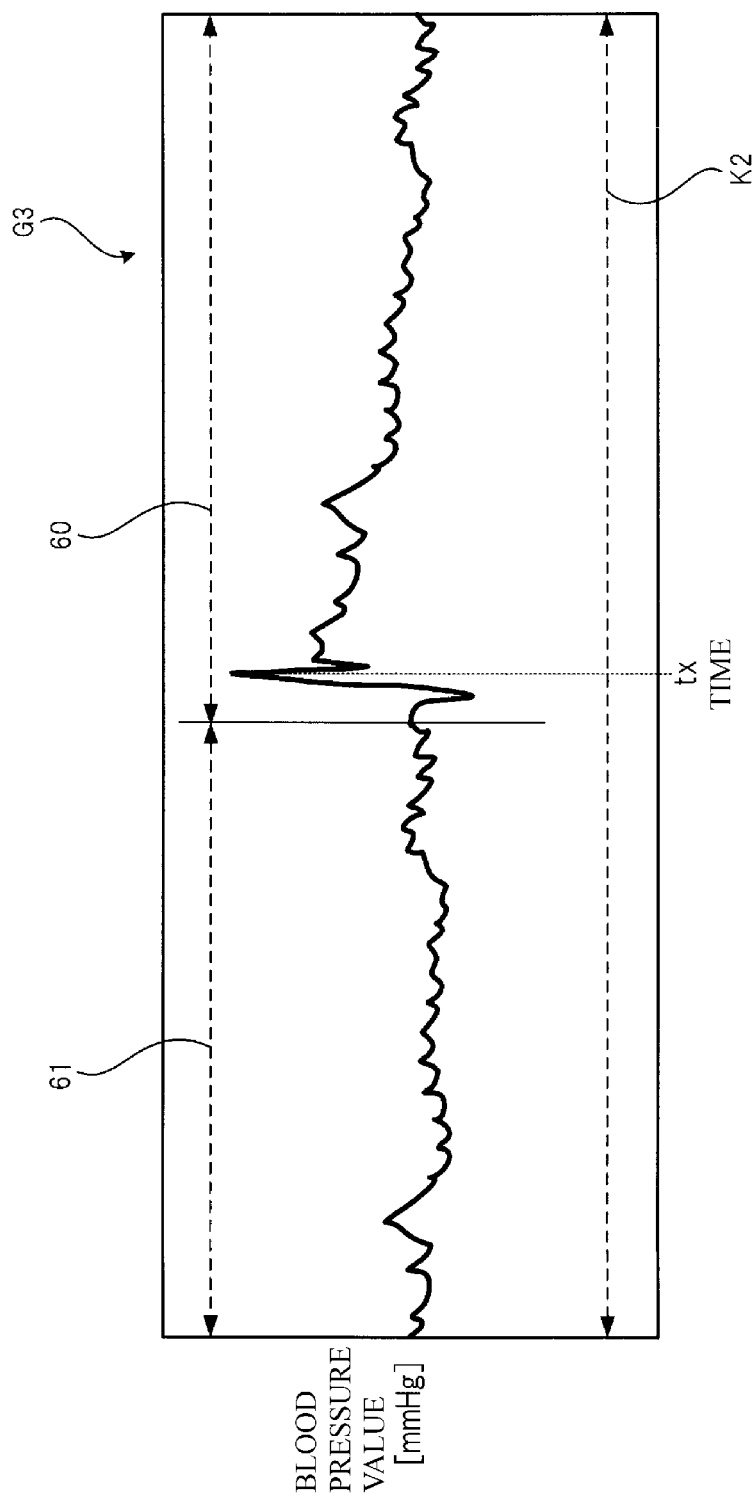
FIG. 9 is a diagram showing an example of display of a second graph G3 showing blood pressure information in a display range H shown in FIG. 8.

FIG. 8 is a diagram showing an example in which a width K2 of the display range set by the display control unit 26 is made wider than the width of a segment K1. FIG. 9 is a diagram showing an example of display of a second graph G3 showing SBPs in the display range H shown in FIG. 8.

In the second graph G3, the SBPs in the range indicated by reference numeral 60 are SBPs in the range corresponding to the image D1 selected by the doctor. In the second graph G3, the SBPs in the range indicated by reference numeral 61 are a portion of the SBPs in the segment adjacent to the left of the segment corresponding to the image D1 selected by the doctor.

In this modified example, the display control unit 26 sets the display range H with the width K2, which is larger than the width of segment K1, such that all of the SBPs in the segment corresponding to the image D1 selected by the doctor are included and the maximum value of the SBPs in this segment are in the center in the display range H.

Accordingly, in the second graph G3, the maximum value of the SBPs in the segment corresponding to the selected image D1 is displayed in the center of the horizontal direction.

It is thought that the doctor first checks a point at which the SBP significantly fluctuates in the selected segment. For this reason, by displaying the second graph G3 centered about this point, it is possible to smoothly check the point portion and diagnosis can be performed efficiently.

Note that as shown in FIGS. 5 and 9, if the second graph including the SBPs of the segment selected by the doctor and the SBPs of another segment is displayed, it is preferable that the display control unit 26 makes the display mode for the SBPs of the segment selected by the doctor and the display mode for the SBPs of the other segment different from each other.

Examples of making the display modes different from each other include a method of changing the colors of the graphs of the SBPs and a method of changing the types (solid line, broken line, one-dot chain line, etc.) of the graphs of the SBPs.

For example, in the example shown in FIG. 9, the SBPs in the range indicated by reference numeral 61 and the SBPs in the range indicated by reference numeral 60 are displayed in different colors from each other, or the SBPs in the range indicated by reference numeral 61 are displayed using broken lines and the SBPs in the range indicated by reference numeral 60 are displayed using solid lines.

Doing so makes it possible for the doctor to easily determine which segment the doctor first selected, and to efficiently advance diagnosis.

Also, if the first graph shown in FIG. 3 and the second graph shown in FIGS. 4, 5, and 9 are displayed together on the same screen, it is preferable that the display control unit 26 displays, in an emphasized manner, the image indicating the fluctuating state information corresponding to the segment including the SBPs displayed as the second graph.

Figure 10:
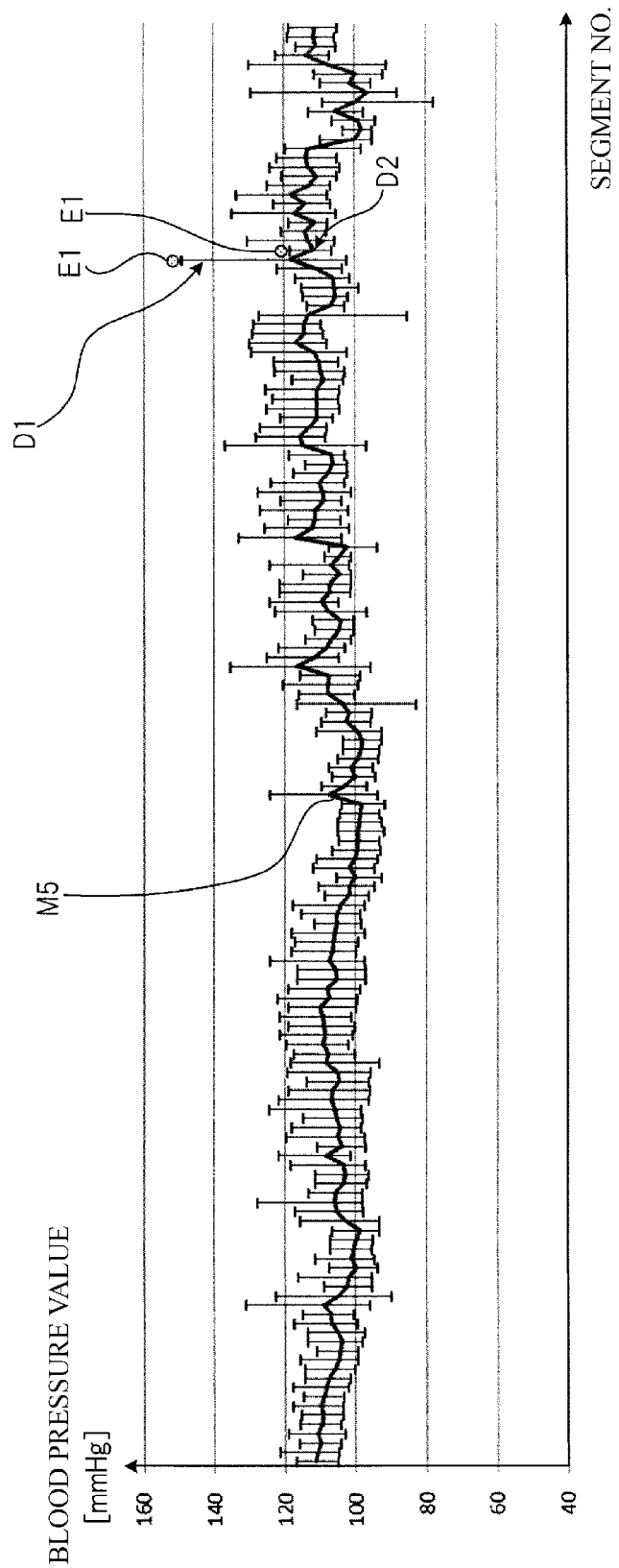
FIG. 10 is a diagram showing a first modified example of a first graph.

FIG. 10 is a diagram showing a first modified example of the first graph.

An exemplary case is given in which the image D1 is selected while the first graph shown in FIG. 10 is displayed, and the second graph G2 shown in FIG. 5 is displayed, for example. In this case, the SBPs in the segment selected by the doctor and the SBPs in the segment adjacent to the right of that segment are displayed on the display unit 27.

For this reason, the display control unit 26 displays, in an emphasized manner, an image D1 and an image D2 indicating the fluctuating state information corresponding to the segment adjacent to the right of the segment corresponding to the image D1.

Specifically, the display control unit 26 displays marks E1 near the image D1 and near the image D2. Alternatively, the display control unit 26 displays the image D1 and the image D2 in colors different from those of the other images indicating fluctuating state information.

Due to performing emphasized display of the image indicating fluctuating state information of the segments belonging to the SBPs being subjected to enlarged display in this manner, the doctor can easily understand which segment in the first graph the enlarged image being displayed belongs to. For this reason, diagnosis can be performed efficiently.

Figure 11:
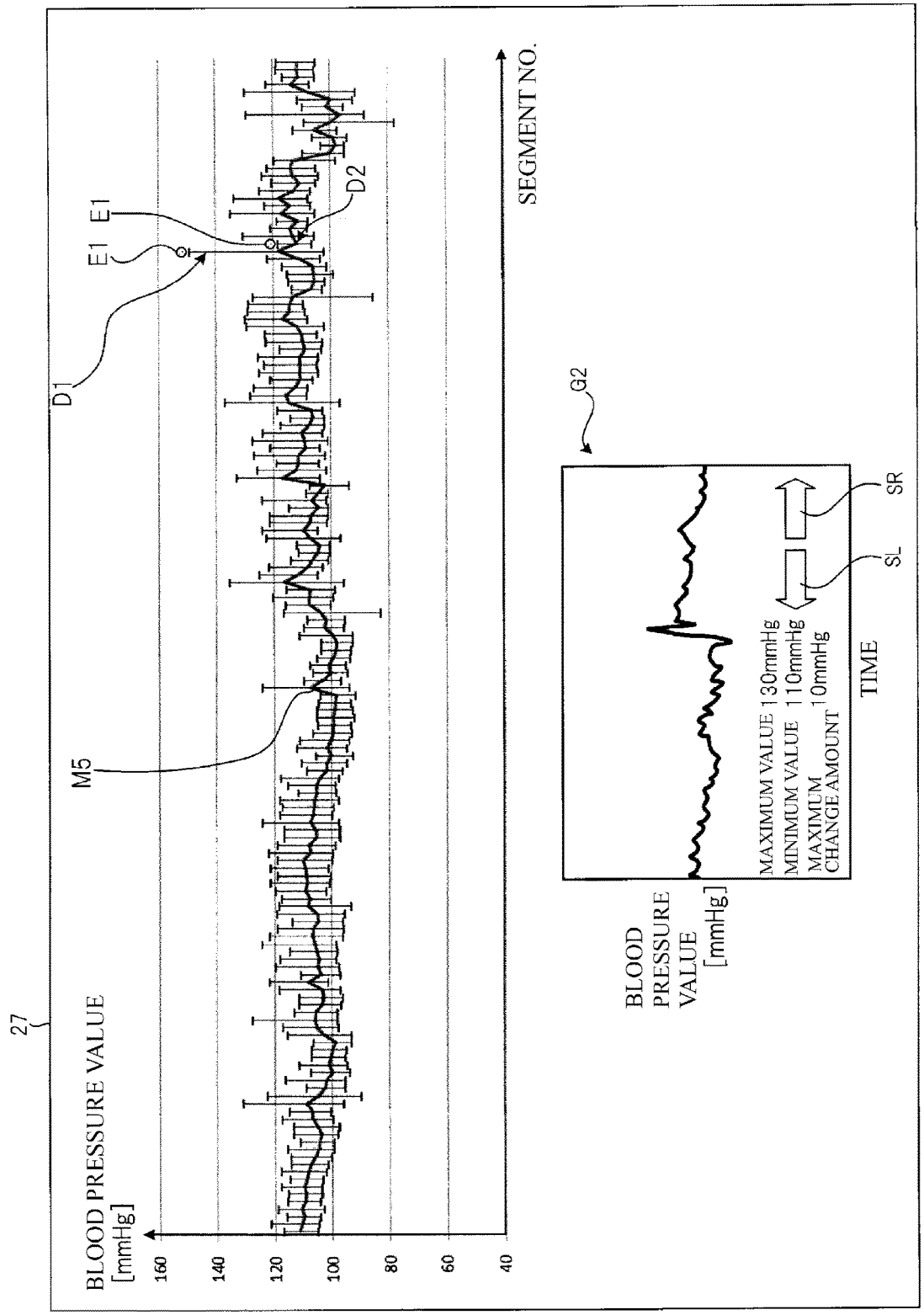
FIG. 11 is a diagram showing an example of displaying both the first graph and the second graph on a display unit 27.

FIG. 11 is a diagram showing an example in which a first graph and a second graph are displayed together on the display unit 27.

An exemplary case is given in which the image D1 is selected while the first graph shown in FIG. 3 is displayed, and thereafter the second graph G2 shown in FIG. 5 for example is displayed according to a scroll operation. In this case, as shown in FIG. 11, the display control unit 26 displays the first graph shown in FIG. 10 and the second graph shown in FIG. 5 on one screen. Accordingly, it is possible to check the overall trend of the blood pressure information and the details of the blood pressure information in a desired segment on the same screen, and thus diagnosis can be performed efficiently.

Figure 12:
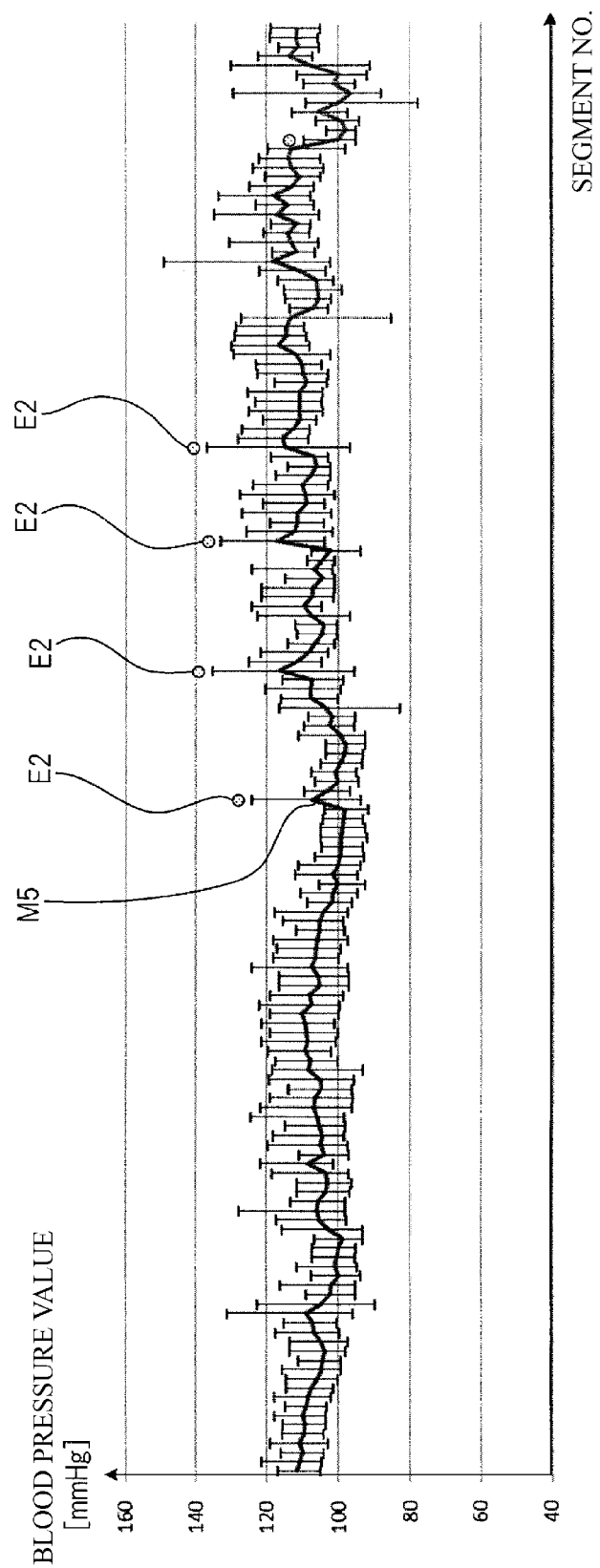
FIG. 12 is a diagram showing a second modified example of a first graph.

FIG. 12 is a diagram showing a second modified example of the first graph.

The display control unit 26 calculates the fluctuation amount (a value obtained by subtracting the average value corresponding to the earlier segment from the average value corresponding to the more recent segment) of the average amount of the blood pressure information constituting the fluctuating state information and performs emphasized display of images corresponding to segments in which the fluctuation amount is greater than or equal to a threshold.

In the example shown in FIG. 12, the display control unit 26 displays marks E2 near images corresponding to segments in which the fluctuation amount of the average value is greater than or equal to a threshold.

If the average value of the blood pressure information suddenly becomes large, it is necessary to suspect that some kind of abnormality has occurred. Due to the marks E2 being displayed as shown in FIG. 12, it is possible to instantaneously understand the locations of the segments in which the fluctuation amount of the average value of the blood pressure information is large, and therefore diagnosis can be performed efficiently.

A configuration may be used in which an image indicating the fluctuating state information can be selected by touching a mark E2 on a touch panel or clicking a mark E2 using a mouse.

In the foregoing description, the biological information calculation unit 11 of the biological information measurement apparatus 1 calculated and stored the blood pressure information as biological information.

The biological information calculation unit 11 may also calculate and store a pulse rate or a heart rate serving as biological information, based on a pulse wave detected by the pulse wave detection unit 10.

As the biological information, it is sufficient to use biological information that significantly fluctuates over the course of a day and is effective for diagnosis when measured every heartbeat or every multiple heartbeats.

Also, an apparatus that measures biological information non-invasively was used as an example of the biological information measurement apparatus 1, but the present invention can similarly be applied also to an apparatus that measures biological information invasively and stores the information.

The fluctuating state information need only be information according to which a fluctuating state in a certain segment of the biological information can be understood, and the representative value may be excluded from the group consisting of the maximum value, the minimum value, and the representative value. Also, the image showing the fluctuating state information is not limited to that illustrated in FIG. 3, and need only be an image according to which it is possible to intuitively understand the fluctuating state.

In the foregoing description, a configuration was used in which when the image D1 is selected while the first graph shown in FIG. 3 is displayed, the second graph indicating the raw data of the blood pressure information is instantaneously displayed.

As a modified example of this, when the image D1 is selected while the first graph shown in FIG. 3 is displayed, the fluctuating state information generation unit 24 acquires the blood pressure information belonging to the segment corresponding to the selected image D1 from the storage medium 23, further divides the acquired blood pressure information into small detailed segments, and once again generates and stores the fluctuating state information for each detailed segment. Note that in this modified example, the blood pressure information acquired from the storage medium 23 (blood pressure information belonging to the segment corresponding to the image D1) constitutes a predetermined period's worth of biological information.

Thereafter, the display control unit 26 displays, on the display unit 27, the first graph indicating the fluctuating state information of each detailed segment generated by the fluctuating state information generation unit 24. In this state, when a certain piece of fluctuating state information in the first graph is selected, the display control unit 26 displays the raw data of the blood pressure information belonging to the detailed segment corresponding to this certain piece of fluctuating state information as the second graph.

Thus, display is not suddenly changed from the first graph to the second graph, but instead the display is changed from the first graph to a first graph in which the widths of the divided segments are smaller, and from this state, the display is changed to the second graph, whereby it is possible to smoothly check the blood pressure information in a long period.

For example, when the fluctuating state information of a certain segment is selected while the first graph, in which the length of a segment is 1 hour, is displayed, the display control unit 26 displays a first graph in which the certain segment is divided into detailed segments of 1 minute. Doing so makes it possible to narrow down the segments to be checked in the enormous amount of blood pressure information and display them in detail, and thus the task of checking the needed information in a large amount of blood pressure information can be performed efficiently.

The embodiments disclosed herein are to be considered in all respects exemplary and not limiting. The scope of the present invention is indicated by the claims and not the above description, and is intended to encompass all modifications within the meaning and range equivalent to the claims.

The diagnosis assistance program of the present embodiment is stored in a computer-readable non-transitory storage medium. Such a "computer-readable storage medium" includes, for example, optical media such as CD-ROMs (Compact Disc-ROMs), magnetic storage media such as memory cards, and the like. Also, this program can be provided through download via a network.

As described above, the following items are disclosed in the present specification.

The disclosed diagnosis assistance apparatus includes: a fluctuating state information generation unit configured to acquire a predetermined period's worth of biological information measured from a living body every heartbeat or every plurality of heartbeats, from a storage unit storing the biological information, divide the acquired predetermined period's worth of biological information into a plurality of segments, and generate fluctuating state information indicating a fluctuating state of the biological information in each segment; and a display control unit configured to display a first graph indicating the fluctuating state information for each segment on a display unit, wherein if a certain piece of the fluctuating state information in the first graph displayed on the display unit is selected, the display control unit sets a display range that is to be displayed on the display unit among the predetermined period's worth of biological information to be a range that includes the biological information belonging to the segment corresponding to the selected piece of the fluctuating state information, and the display control unit displays a second graph indicating the biological information in the set display range in a time series on the display unit.

With the disclosed diagnosis assistance apparatus, if an instruction to move the display range is given while the second graph is displayed on the display unit, the display control unit performs scroll display of the second graph by updating the setting of the display range in accordance with the instruction.

With the disclosed diagnosis assistance apparatus, the display control unit determines a degree of similarity between the selected piece of the fluctuating state information and fluctuating state information in a segment adjacent to the segment including the biological information being displayed as the second graph, and if there is an adjacent segment for which the degree of similarity is greater than or equal to a threshold, the display control unit displays information for performing notification of the direction of that segment in addition to the second graph.

With the disclosed diagnosis assistance apparatus, the display control unit sets the display range such that a maximum value among the biological information belonging to the segment corresponding to the selected piece of the fluctuating state information is located at the center of the second graph.

With the disclosed diagnosis assistance apparatus, the display control unit displays both the first graph and the second graph on the display unit and furthermore performs control for emphasizing the fluctuating state information of the segment to which the biological information being displayed as the second graph belongs, among the fluctuating state information of the first graph.

With the disclosed diagnosis assistance apparatus, the display control unit sets a range wider than the width of the segment as the display range.

With the disclosed diagnosis assistance apparatus, regarding the biological information of the second graph, the display control unit displays the biological information belonging to the segment corresponding to the selected piece of the fluctuating state information and the biological information belonging to another segment with display styles that are different from each other.

With the disclosed diagnosis assistance apparatus, the fluctuating state information generation unit generates an image indicating a difference between a maximum value and a minimum value of the biological information in each segment as the fluctuating state information.

With the disclosed diagnosis assistance apparatus, the fluctuating state information generation unit generates an image indicating differences between a representative value and a maximum value and minimum value of the biological information in each segment as the fluctuating state information.

With the disclosed diagnosis assistance apparatus, the biological information is blood pressure information.

The disclosed diagnosis assistance method includes: a fluctuating state information generation step of acquiring a predetermined period's worth of biological information measured from a living body every heartbeat or every plurality of heartbeats, from a storage unit storing the biological information, dividing the acquired predetermined period's worth of biological information into a plurality of segments, and generating fluctuating state information indicating a fluctuating state of the biological information in each segment; and a display control step of displaying a first graph indicating the fluctuating state information for each segment on a display unit, wherein in the display control step, if a certain piece of the fluctuating state information in the first graph displayed on the display unit is selected, a display range that is to be displayed on the display unit among the predetermined period's worth of biological information is set to be a range that includes the biological information belonging to the segment corresponding to the selected piece of the fluctuating state information, and a second graph indicating the biological information in the set display range in a time series is displayed on the display unit.

The disclosed diagnosis assistance program is for causing a computer to execute: a fluctuating state information generation step of acquiring a predetermined period's worth of biological information measured from a living body every heartbeat or every plurality of heartbeats, from a storage unit storing the biological information, dividing the acquired predetermined period's worth of biological information into a plurality of segments, and generating fluctuating state information indicating a fluctuating state of the biological information in each segment; and a display control step of displaying a first graph indicating the fluctuating state information for each segment on a display unit, wherein in the display control step, if a certain piece of the fluctuating state information in the first graph displayed on the display unit is selected, a display range that is to be displayed on the display unit among the predetermined period's worth of biological information is set to be a range that includes the biological information belonging to the segment corresponding to the selected piece of the fluctuating state information, and a second graph indicating the biological information in the set display range in a time series is displayed on the display unit.

A diagnosis assistance apparatus of the present invention includes: a fluctuating state information generation unit configured to acquire a predetermined period's worth of biological information measured from a living body every heartbeat or every plurality of heartbeats, from a storage unit storing the biological information, divide the acquired predetermined period's worth of biological information into a plurality of segments, and generate fluctuating state information indicating a fluctuating state of the biological information in each segment; and a display control unit configured to display the fluctuating state information for each segment on a display unit, wherein, if a certain piece of the fluctuating state information displayed on the display unit is selected, the display control unit sets the display range that is to be displayed on the display unit among the predetermined period's worth of biological information to be a range that includes the biological information belonging to the segment corresponding to the selected piece of the fluctuating state information, and the display control unit displays the biological information in the set display range on the display unit.

A diagnosis assistance method of the present invention includes: a fluctuating state information generation step of acquiring a predetermined period's worth of biological information measured from a living body every heartbeat or every plurality of heartbeats, from a storage unit storing the biological information, dividing the acquired predetermined period's worth of biological information into a plurality of segments, and generating fluctuating state information indicating a fluctuating state of the biological information in each segment; and a display control step of displaying the fluctuating state information for each segment on a display unit, wherein, in the display control step, if a certain piece of the fluctuating state information displayed on the display unit is selected, the display range that is to be displayed on the display unit among the predetermined period's worth of biological information is set to be a range that includes the biological information belonging to the segment corresponding to the selected piece of the fluctuating state information, and the biological information in the set display range is displayed on the display unit.

A diagnosis assistance program of the present invention is a diagnosis assistance program for causing a computer to execute: a fluctuating state information generation step of acquiring a predetermined period's worth of biological information measured from a living body every heartbeat or every plurality of heartbeats, from a storage unit storing the biological information, dividing the acquired predetermined period's worth of biological information into a plurality of segments, and generating fluctuating state information indicating a fluctuating state of the biological information in each segment; and a display control step of displaying the fluctuating state information for each segment on a display unit, wherein, in the display control step, if a certain piece of the fluctuating state information displayed on the display unit is selected, the display range that is to be displayed on the display unit among the predetermined period's worth of biological information is set to be a range that includes the biological information belonging to the segment corresponding to the selected piece of the fluctuating state information, and the biological information in the set display range is displayed on the display unit.

According to the present invention, it is possible to provide a diagnosis assistance apparatus, a diagnosis assistance method, and a diagnosis assistance program that can efficiently perform assistance of diagnosis based on biological information measured in units of heartbeats.

INDUSTRIAL APPLICABILITY

The present invention can contribute to medical treatment by assisting diagnosis.

Although the present invention has been described above by means of specific embodiments, the present invention is not limited to the embodiments, and various modifications are possible without departing from the technical gist of the disclosed invention.

REFERENCE SIGNS LIST

1 Biological information measurement apparatus
2 Diagnosis assistance apparatus
23 Storage medium (storage unit)
24 Fluctuating state information generation unit
26 Display control unit
27 Display unit
K1 Segment
H Display range
D1 Image indicating fluctuating state information
G1, G2, G3 Second graph
SL, SR Scroll button
E1, E2 Mark

The invention claimed is:

1. A diagnosis assistance apparatus comprising:
a display screen; and
a processor programmed to:
  acquire, from a memory, blood pressure information in a predetermined period for a living body,
  divide the acquired blood pressure information into a plurality of segments,
  generate fluctuating state information composed of a maximum value, a minimum value, and a representative value of the blood pressure information in each segment,
  display, on the display screen, a first graph indicating positions of the maximum value, the minimum value, and the representative value of the blood pressure information in each segment and a vertical bar connecting the positions,
  receive an input that selects a piece of the fluctuating state information from the acquired blood pressure information,
  set blood pressure information in a display range that includes the selected piece of the fluctuating state information based on the received input, and
  display, on the display screen, a second graph indicating the blood pressure information in the display range in a time series.

2. The diagnosis assistance apparatus according to claim 1, wherein the processor performs scroll display of the second graph by updating the setting of the display range in accordance with the instruction in response to an instruction to move the display range while the second graph is displayed on the display screen.

3. The diagnosis assistance apparatus according to claim 2, wherein
  the processor determines a degree of similarity between the selected piece of the fluctuating state information and fluctuating state information in a different segment adjacent to the segment including the blood pressure information being displayed in the second graph, and
  the processor displays a notification of a direction of the different segment in response to the determined degree of similarity being greater than or equal to a predetermined threshold.

4. The diagnosis assistance apparatus according to claim 1, wherein the processor sets the display range such that a maximum value in the selected piece of the fluctuating state information is located at a center of the second graph.

5. The diagnosis assistance apparatus according to claim 1, wherein
  the processor simultaneously displays the first graph and the second graph on the display screen, and
  the processor performs control for emphasizing the selected piece of the fluctuating state information, among the fluctuating state information of the first graph.

6. The diagnosis assistance apparatus according to claim 1, wherein the processor sets a range wider than the width of the segment as the display range.

7. The diagnosis assistance apparatus according to claim 6, wherein the processor displays the blood pressure information in the selected piece of the fluctuating state information and the blood pressure information belonging to another segment with display styles that are different from each other.

8. A diagnosis assistance method comprising:
  acquiring, from a memory, blood pressure information in a predetermined period for a living body,
  dividing the acquired blood pressure information into a plurality of segments,
  generating fluctuating state information composed of a maximum value, a minimum value, and a representative value of the blood pressure information in each segment,
  displaying, on a display screen, a first graph indicating positions of the maximum value, the minimum value, and the representative value of the blood pressure information in each segment and a vertical bar connecting the positions,
  receiving an input that selects a piece of the fluctuating state information from the acquired blood pressure information,
  setting blood pressure information in a display range that includes the selected piece of the fluctuating state information based on the received input, and
  displaying, on the display screen, a second graph indicating the blood pressure information in the display range in a time series.

9. A non-transitory computer readable medium storing a diagnosis assistance program that causes a computer to execute steps comprising:
  acquiring, from a memory, blood pressure information in a predetermined period for a living body,
  dividing the acquired blood pressure information into a plurality of segments, generating fluctuating state information composed of a maximum value, a minimum value, and a representative value of the blood pressure information in each segment, displaying, on a display screen, a first graph indicating positions of the maximum value, the minimum value, and the representative value of the blood pressure information in each segment and a vertical bar connecting the positions, receiving an input that selects a piece of the fluctuating state information from the acquired blood pressure information, setting blood pressure information in a display range that includes the selected piece of the fluctuating state information based on the received input, and displaying, on the display screen, a second graph indicating the blood pressure information in the display range in a time series.

10. A diagnosis assistance apparatus comprising:
a display screen; and
a processor programmed to:
  acquire, from a memory, biological information in a predetermined period for a living body,
  divide the acquired biological information into a plurality of segments,
  generate fluctuating state information indicating a fluctuating state of the biological information in each segment,
  display, on the display screen, a first graph indicating the fluctuating state information for each segment,
  receive an input that selects a piece of the fluctuating state information from the acquired blood pressure information,
  set blood pressure information in a display range that includes the selected piece of the fluctuating state information based on the received input,
  display, on the display screen, a second graph indicating the biological information in the set display range in a time series, and
  set the display range such that a maximum value in the selected piece of the fluctuating state information is located at a center of the second graph.

11. A diagnosis assistance method comprising:
acquiring, from a memory, biological information in a predetermined period for a living body, dividing the acquired biological information into a plurality of segments, generating fluctuating state information indicating a fluctuating state of the biological information in each segment, displaying, on a display screen, a first graph indicating the fluctuating state information for each segment, receiving an input that selects a piece of the fluctuating state information from the acquired blood pressure information, setting blood pressure information in a display range that includes the selected piece of the fluctuating state information based on the received input, displaying, on the display screen, a second graph indicating the biological information in the set display range in a time series, and setting the display range such that a maximum value in the selected piece of the fluctuating state information is located at a center of the second graph.

12. A non-transitory computer readable medium storing a diagnosis assistance program that causes a computer to execute steps comprising:
  acquiring, from a memory, biological information in a predetermined period for a living body,
  dividing the acquired biological information into a plurality of segments,
  generating fluctuating state information indicating a fluctuating state of the biological information in each segment,
  displaying, on a display screen, a first graph indicating the fluctuating state information for each segment,
  receiving an input that selects a piece of the fluctuating state information from the acquired blood pressure information,
  setting blood pressure information in a display range that includes the selected piece of the fluctuating state information based on the received input,
  displaying, on the display screen, a second graph indicating the biological information in the set display range in a time series, and
  setting the display range such that a maximum value in the selected piece of the fluctuating state information is located at a center of the second graph.

* * * * *